US00PP16191P2

(12) United States Plant Patent
Olesen et al.

(10) Patent No.: US PP16,191 P2
(45) Date of Patent: Jan. 10, 2006

(54) ***CLEMATIS* PLANT NAMED 'EVIPO021'**

(50) Latin Name: *Clematis viticella*
Varietal Denomination: EVIpo021

(75) Inventors: Mogens N. Olesen, Fredensborg (DK); Raymond J. Evison, St. Sampsons (GB)

(73) Assignee: Poulsen Roser A/S, Fredensborg (DK)

( * ) Notice: Subject to any disclaimer, the term of this patent is extended or adjusted under 35 U.S.C. 154(b) by 155 days.

(21) Appl. No.: 10/886,290

(22) Filed: Jul. 6, 2004

(51) Int. Cl.
*A01H 5/00* (2006.01)

(52) U.S. Cl. ..... Plt./228
(58) Field of Classification Search ..... Plt./228
See application file for complete search history.

*Primary Examiner*—Kent Bell

(57) ABSTRACT

A new *Clematis* cultivar which is well suited to propagation in glasshouses with a tall growth habit, profuse, pink flowers, and continuous summer flowering. The variety successfully propagates from softwood cuttings and is suitable for cultivation in commercial glasshouses. This new and distinct variety has shown to be uniform and stable in the resulting generations from asexual propagation.

2 Drawing Sheets

Botanical classification: Genus—*Clematis*. Species—*viticella*.

Variety denomination: 'EVIpo21'.

Commercial classification: Early flowering cultivar.

SUMMARY OF THE INVENTION

The present invention constitutes a new and distinct variety of *Clematis* which originated from a controlled crossing between the female parent, 'Mrs. George Jackman', a non-patented cultivar, and the male parent, 'Dr. Ruppel', a non-patented cultivar.

The new *clematis* may be distinguished from its female seed parent, 'Mrs. George Jackman', by the following combination of characteristics:

1. Flowers of 'EVIpo021' exhibit pink tones while those of 'Mrs. Geroge Jackman' are purely white.

The new *clematis* may be distinguished from its male pollen parent, 'Dr. Ruppel', by the following combination of characteristics:

1. 'EVIpo021' has smaller flowers.
2. Flower color of 'EVIpo021' has less red coloration.

The seed resulting from the cross pollination of the parent varieties was planted in a controlled environment. The resulting seedlings were evaluated. The new variety, 'EVIpo021', was selected among those seedlings. The objective of the selection of this *Clematis* variety for commercial glasshouse and nursery culture was to create a new and distinct variety with unique qualities that this variety has:

1. Good repeat flowering habit.
2. Light pink flowers.
2. Suitable for small container culture.

These qualities required improvement in *Clematis* varieties that were in commercial cultivation and the objectives have been substantially achieved in the new variety, as evidenced by the unique combination of characteristics that are present in 'EVIpo021' which distinguish it from all other varieties of which we are aware.

The seeds from the aforementioned hybridization were germinated and evaluations of the resulting seedling plants were conducted in a controlled environment. As a result, 'EVIpo021' was selected by Raymond J. Evison and Mogens N. Olesen in their *Clematis* development program in Domarie Vineries Les Sauvagees, St. Sampsons, Guernsey, Channel Islands, United Kingdom in April 1998.

Asexual reproduction of 'EVIpo021' by cuttings was first done by Raymond J. Evison and Mogens N. Olesen in Domarie Vineries Les Sauvagees, St. Sampsons, Guernsey, Channel Islands, United Kingdom in May 1998. This initial and subsequent asexual propagations have demonstrated that the characteristics of 'EVIpo021' are true to type and are transmitted from one generation to the next.

BRIEF DESCRIPTION OF THE DRAWING

The accompanying color illustrations show as true as is reasonably possible to obtain in color photographs of this type:

FIG. 1.2 Mature leaves;

FIG. 1.3 Stem, leaves, bud at ¼ opening, bud closed;

FIG. 1.4 Open flower upper and lower view;

DETAILED DESCRIPTION OF THE VARIETY

Figure 1:
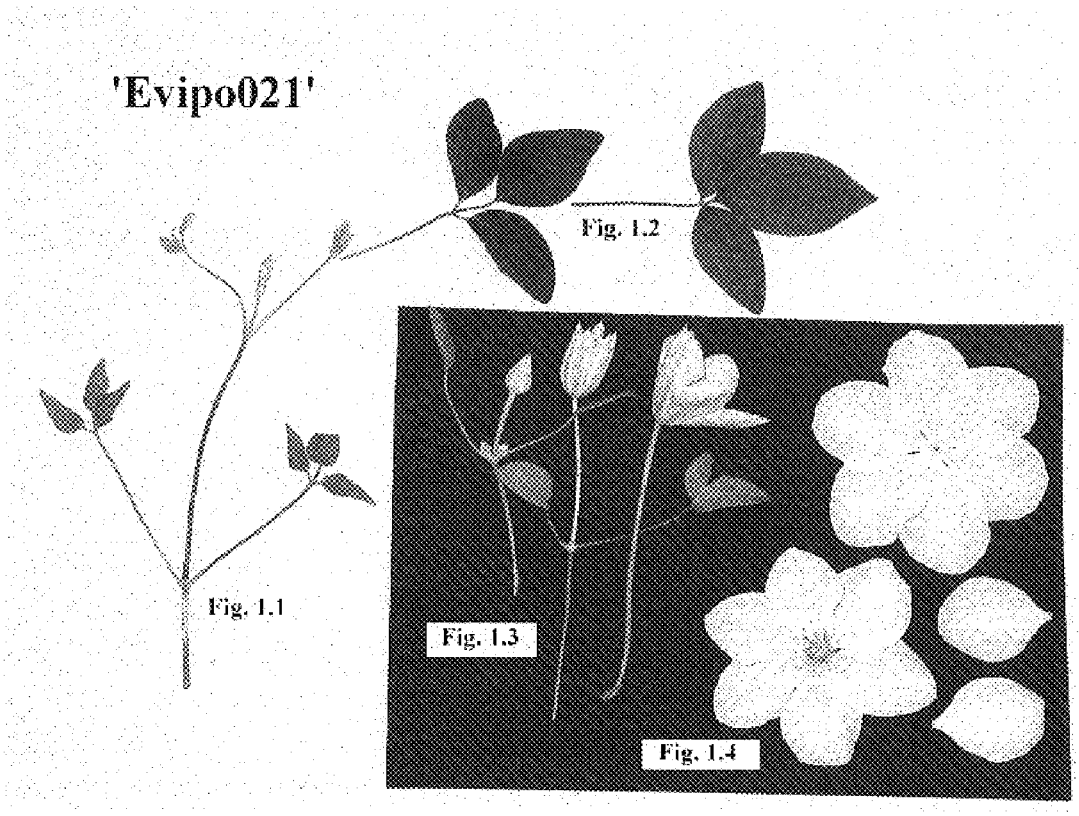
FIG. 1.1 Juvenile growth.
Figure 2:
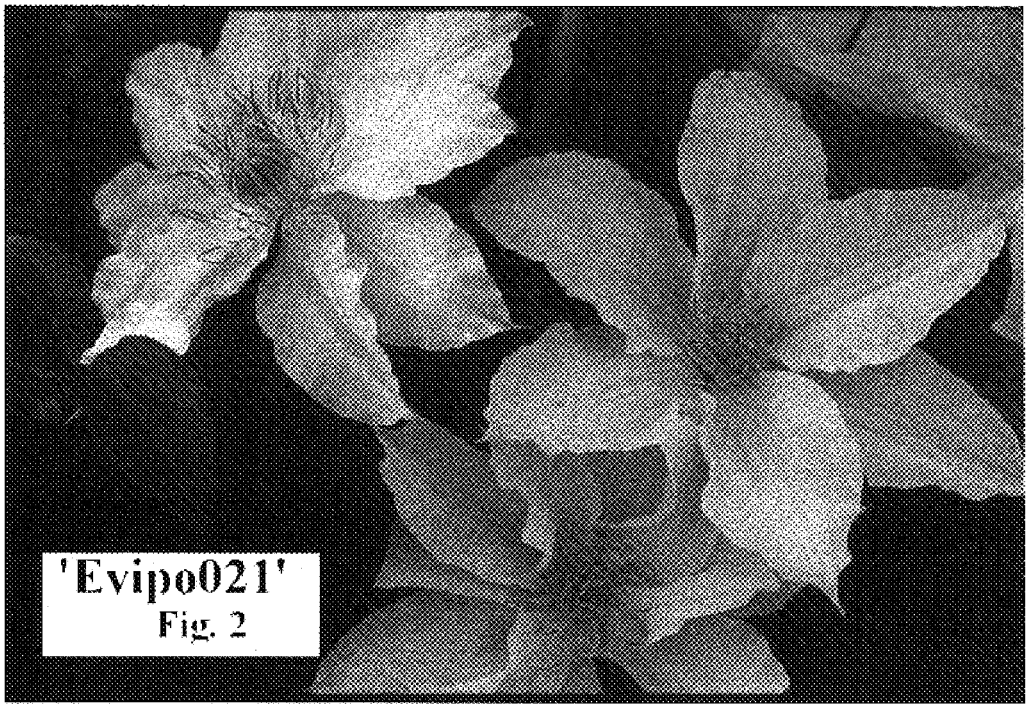
FIG. 2 Open flowers.

The following is a detailed description of 'EVIpo021', as observed in its growth throughout the flowering period in glasshouses at Domarie Vineries Les Sauvagees, St. Sampsons, Guernsey, Channel Islands, United Kingdom. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 1995.

For a comparison, the nearest existing *Clematis* variety is 'EVIpo017', described and illustrated in U.S. Plant Pat. No. 15,163 and dated Sep. 21, 2004. Chart 1 details several physical characteristics of 'EVIpo021' and the comparison variety.

CHART 1

| | 'EVIpo021' | 'EVIpo017' |
|---|---|---|
| Tepal main color | Light Purple RHS 75D. | Violet RHS85B. |
| Tepal arrangement/count | Normally 6–10 outer tepals with some inner petaloid stamens (semi-double). | Normally 6–10 tepals arranged regularly. |

FLOWER AND FLOWER BUD

Blooming habit: Recurrent. Flowering period normally Spring from April to May. Flowering occurs again in Autumn from September to October. Flowering may be continuous if vines are pruned accordingly.

Flower bud:

*Size.*—30 to 40 mm in length. Bud diameter is 20 mm.

*Bud form.*—Broad based ovoid.

*Bud color.*—Green Group 138C. Tepals are Red-Purple Group 75D at ¼ opening.

Peduncle:

*Surface.*—Smooth.

*Length.*—60–90 mm.

*Color.*—Green Group 137C.

*Strength.*—Strong.

Receptacle: Absent.

Flower arrangement:

*Location on vine.*—New and old growth.

*Borne.*—Singly or in Clusters of 3–7 flowers.

Flower bloom:

*Size.*—100–130 mm in diameter. 25 mm in depth.

*Profile.*—Upon opening: Flowers are flat. Open: Flowers are flat with straight tepals.

*Tepal color.*—Upon opening: Upper surface is Purple Group 75C with a darker bar Purple Group 75A in color. After opening: Upper surface is Purple Group 75D with a central bar Purple Group 75B in color. Lower surface about same as upper surface.

*Variations.*—Uniform.

*Fragrance.*—None.

*Lasting quality on plant.*—10–20 days.

*Lasting quality as a cut flower.*—1–4 days.

Tepals:

*Quantity.*—Usually single but on occasions semi-Double. Average range is 6 to 10 tepals.

*Size.*—50–65 mm in length by 25–35 mm wide.

*Shape.*—Individual tepal shape is ovate.

*Cross section.*—Flat.

*Margins.*—Entire. Undulation of margin: Weak. Tepal apex: Mucronate. Recurvature of tip: Slightly curved. Persistence: Tepals drop off cleanly. Arrangement: Tepals are arranged regularly when single and informally when semi-double.

Reproductive organs:

*Arrangement.*—Open.

*Pollen.*—Quantity: Normal quantity. Color: Yellow Group 4D.

*Anthers.*—Size: 7–10 mm in length. Color: Red-Purple 72B Group. Quantity: 80 to 90.

*Filaments.*—Color: White Group 155A. Length: 10 to 12 mm.

*Pistils.*—Quantity: 70 to 80.

*Stigmas.*—Inferior becoming superior in location relative to the length of the filaments and the height of the anthers as the flower opens.

*Styles.*—Color: Yellow Group 2D. Length: 12 to 18 mm.

Seed head characteristics: Overall seed head is globular. Individual seed: Size: 5 to 7 mm diameter at the base with a long 30 to 45 mm plumule. Shape: Circular to tear shape with plumule.

*Style appearance.*—Feathery. 50 to 80 mm in length.

PLANT

Plant form: Climbing.

Plant growth: Seasons growth attains 1.0 to 1.5 meters in height. Average spread is 500 cm.

Hardiness: Trials to date show the variety is tolerant to USDA cold hardiness zone 4.

Stems:

*Color.*—Young wood: Yellow-Green Group 144A, becoming Greyed-Orange Group 173A. Older wood: Brown Group 200B.

*Internodes.*—Shape: Cylindrical. Length: 80 to 150 mm.

*Surface.*—Young wood: Smooth, slightly pubescent. Older wood: Smooth.

Plant foliage:

*Leaf characteristics.*—Deciduous.

*Mature leaf form.*—Simple or trifoliate. Normally 3 leaflets.

*Compound leaf size.*—150 to 200 mm (l)×80 to 120 mm(w).

*Abundance.*—Generally, there are 4 leaves per 80 to 150 mm of stem.

*Color of mature leaves.*—Upper: Green Group 137B. Lower: Green Group 138B.

*Color of juvenile foliage.*—Upper: Green Group 143A. Lower: Green Group 143B.

Plant leaves and leaflets:

*Stipules.*—Absent.

*Perioles.*—Average length: 60 to 90 mm. Color: Yellow-Green Group 144A turning Greyed-Orange Group 173A. Clasping: By leaf petiole.

*Petioloule.*—Length: 10 to 12 mm. Color: Yellow-Green Group 144A aging to Greyed-Orange Group 173A.

*Leaf edge.*—Terminal leaflet margin is entire. Lobes are rounded.

*Leaflet shape.*—General shape: Ovate to elliptic. Base: Rounded. Apex: Acute.

*Margin.*—Entire.

*Leaflet size.*—55 to 70 mm in length by 30 to 45 mm wide.

*Texture.*—Smooth.

*Surface.*—Upper side: Smooth. Lower side: Smooth.

*Thickness.*—Moderate.

*Glossiness.*—Moderately Glossy.

Disease resistance: Subject to any disease that normally attacks the species.

We claim:

1. A new and distinct variety of *clematis* plant named 'EVIpo021', described and illustrated herein as a distinct and novel *clematis* variety due to its abundant pink flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

'Evipo021'
Fig. 1.2
Fig. 1.1
Fig. 1.3
Fig. 1.4

'Evipo021'